(12) United States Patent
Kita et al.

(10) Patent No.: US 8,900,830 B2
(45) Date of Patent: Dec. 2, 2014

(54) PROCESS FOR PRODUCING OPTICALLY ACTIVE SUCCINIMIDE DERIVATIVES

(75) Inventors: Shinji Kita, Toyama (JP); Kazuya Tsuzaki, Toyama (JP); Eitora Yamamura, Toyama (JP)

(73) Assignees: Sumitomo Dainippon Pharma Co., Ltd., Osaka (JP); Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 13/812,782

(22) PCT Filed: Jul. 28, 2011

(86) PCT No.: PCT/JP2011/067192
§ 371 (c)(1),
(2), (4) Date: Mar. 27, 2013

(87) PCT Pub. No.: WO2012/014953
PCT Pub. Date: Feb. 2, 2012

(65) Prior Publication Data
US 2013/0196388 A1 Aug. 1, 2013

(30) Foreign Application Priority Data

Jul. 29, 2010 (JP) ................................ 2010-170349

(51) Int. Cl.
| | | |
|---|---|---|
| C12P 13/04 | (2006.01) | |
| C12P 17/18 | (2006.01) | |
| C12P 17/10 | (2006.01) | |
| C12P 7/62 | (2006.01) | |
| C12N 9/16 | (2006.01) | |
| C12N 9/18 | (2006.01) | |
| C07H 21/04 | (2006.01) | |
| C07K 1/00 | (2006.01) | |
| C07D 207/416 | (2006.01) | |
| C12P 41/00 | (2006.01) | |
| C07D 487/20 | (2006.01) | |
| C12P 7/46 | (2006.01) | |

(52) U.S. Cl.
CPC . *C12P 17/10* (2013.01); *C12N 9/18* (2013.01); *C07D 207/416* (2013.01); *C12P 41/005* (2013.01); *C07D 487/20* (2013.01); *C12P 7/46* (2013.01)
USPC ........... 435/106; 435/119; 435/121; 435/135; 435/196; 435/197; 536/23.2; 530/350

(58) Field of Classification Search
USPC ................ 435/106, 119, 121, 135, 196, 197; 536/23.2; 530/350
See application file for complete search history.

(56) References Cited

U.S. PATENT DOCUMENTS

| 8,633,001 B2 * | 1/2014 | Kasai et al. ................... 435/121 |
| 2010/0003729 A1 | 1/2010 | Kudo et al. |

FOREIGN PATENT DOCUMENTS

| JP | 05-186472 A | 7/1993 |
| JP | 06-192222 A | 7/1994 |
| JP | 10-245369 A | 9/1998 |
| WO | WO 2008/035735 A1 | 3/2008 |

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

(Continued)

*Primary Examiner* — Ganapathirama Raghu
(74) *Attorney, Agent, or Firm* — Leydig, Voit & Mayer, Ltd.

(57) ABSTRACT

A process for efficiently producing optically active succinimide derivatives as key intermediates of (3R)-2'-(4-bromo-2-fluorobenzyl)spiro{pyrrolidine-3,4'(1'H)-pyrrolo[1,2-a]pyrazine}-1',2,3',5(2'H)-tetraone, which comprises the following reaction steps, and the step 2 is performed by using a non-animal-derived enzyme.

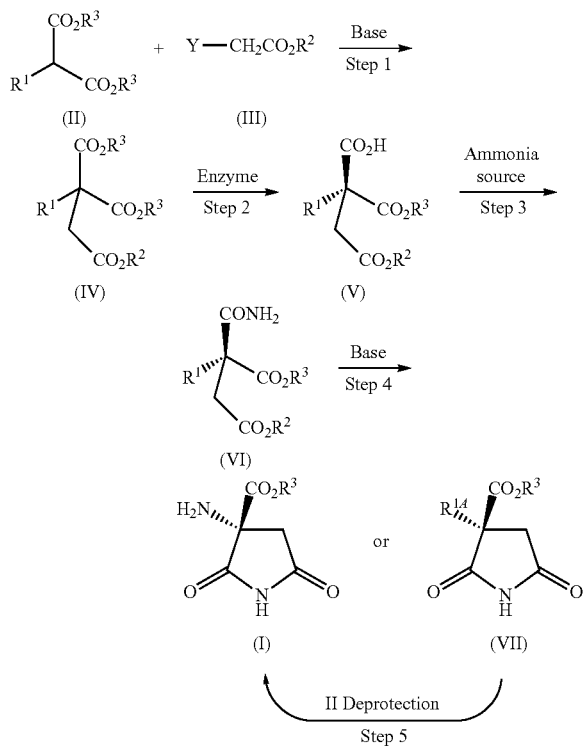

18 Claims, No Drawings

(56) References Cited

OTHER PUBLICATIONS

Devos et al., Practical limits of function prediction. Proteins: Structure, Function, and Genetics. 2000, vol. 41: 98-107.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Haberhauer et al., *Tetrahedron Letters*, 41 (26): 5013-5016 (2000).

Negoro et al., *J. Med. Chem.*, 41 (21): 4118-4129 (1998).

Read et al., "*Bacillus thuringiensis* IBL 200 contig00202, whole genome shotgun sequence," GenBank [online] Accession No. ACNK01000123 (Apr. 30, 2009) [retrieved on Oct. 4, 2011, from internet at http://www.ncbi.nlm.nih.gov/nuccore/ACNK01000123?].

Sano et al., Tetrahedron Letters, 39 (31): 5571-5574 (1998).

Japenese Patent Office, International Search Report in International Patent Application No. PCT/JP2007/068267 (Oct. 23, 2007).

The International Bureau of WIPO, International Preliminary Report in International Patent Application No. PCT/JP2011/067192 (Feb. 7, 2013).

* cited by examiner

PROCESS FOR PRODUCING OPTICALLY ACTIVE SUCCINIMIDE DERIVATIVES

CROSS-REFERENCE TO RELATED APPLICATIONS

This patent application is a U.S. national phase of International Patent Application No. PCT/JP2011/067192, filed on Jul. 28, 2011, which claims the benefit of Japanese Patent Application No. 2010-170349, filed Jul. 29, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,466 bytes ASCII (Text) file named "712171SequenceListing.txt," created Jan. 28, 2013.

TECHNICAL FIELD

The present inventions relates to a process for producing optically active succinimide derivatives as key intermediates of (3R)-2'-(4-bromo-2-fluorobenzyl)spiro{pyrrolidine-3,4'(1'H)-pyrrolo[1,2-a]pyrazine}-1',2,3',5(2'H)-tetraone (henceforth referred to as "compound A" in this specification) represented by the following formula, which is expected to be a therapeutic agent for diabetic complications.

[Formula 1]

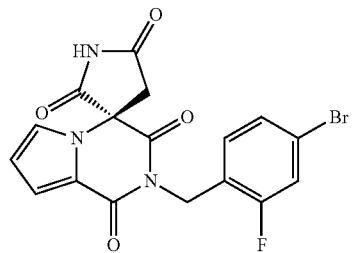

(Compound A)

The present invention also relates to a process for producing optically active carboxylic acid derivatives, which are useful intermediates of the compound A mentioned above, a process for producing the compound A by using said optically active carboxylic acid derivatives, as well as an enzyme having an activity of generating the optically active carboxylic acid derivatives, and a DNA encoding said enzyme.

BACKGROUND ART

Methods for dividing a racemate into optical isomers (optical resolution methods) include a method of using an enzyme, a method of reacting optical isomers for conversion into salts and dividing the salts, a method of preparing a diastereomer mixture by reactions with optical isomers and then purifying the mixture for separation, and the like. Among them, the method of using an enzyme does not require optical isomers, and accordingly the method is advantageous since the reaction can be performed at low cost, for example. However, said method also has a problem that it is generally difficult to regioselectively and stereoselectively hydrolyze a specific alkoxycarbonyl of a triester or the like having two or more alkoxycarbonyls in a single molecule.

As methods for producing an optically active carboxylic acid derivative by regioselective and stereoselective hydrolysis using an esterase, Patent document 1 and Non-patent documents 1 and 2 report methods of asymmetrically hydrolyzing an α-(lower alkyl)-α-(protected amino)malonate diester derivative by using a pig liver esterase to produce an optically active α-(lower alkyl)-α-(protected amino)malonate monoester derivative.

[Formula 2]

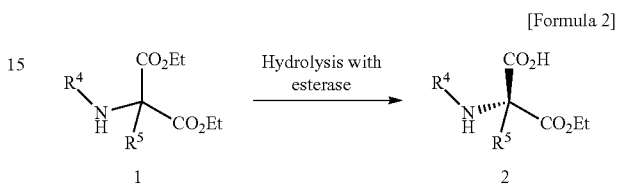

(In the formulas, $R^4$ represents benzyloxycarbonyl, tert-butoxycarbonyl, or the like, and $R^5$ represents a lower alkyl or the like.)

Patent document 2 describes a method for producing (R)-2-amino-2-ethoxycarbonylsuccinimide (henceforth referred to as compound B), which is a key intermediate of the compound A, by using an esterase.

Methods for preparing the compound A from the compound B are described in Patent document 3, Non-patent document 3, and the like, and a method of preparing 4-tert-butyl 1-ethyl 2-benzyloxycarbonylamino-2-ethoxycarbonylsuccinate by reacting diethyl 2-benzyloxycarbonylaminomalonate and tert-butyl 2-bromoacetate is described in Reference Example 1 of Patent document 4.

PRIOR ART REFERENCES

Patent Documents

Patent document 1: Japanese Patent Unexamined Publication (Kokai) No. 10-245369
Patent document 2: International Patent Publication WO2008/035735
Patent document 3: Japanese Patent Unexamined Publication No. 05-186472
Patent document 4: Japanese Patent Unexamined Publication No. 06-192222

Non-Patent Documents

Non-patent document 1: Tetrahedron Letters (Tetrahedron Lett.), 1998, 39 (31), 5571-5574
Non-patent document 2: Tetrahedron Lett., 2000, 41 (26), 5013-5016
Non-patent document 3: Journal of Medicinal Chemistry (J. Med. Chem.), 1998, 41, pp. 4118-4129

SUMMARY OF THE INVENTION

Object to be Achieved by the Invention

An object of the present invention is to provide a process for producing optically active succinimide derivatives as key intermediates of the compound A.

More specifically, the object of the present invention is to provide a process for efficiently producing optically active succinimide derivatives, which are key intermediates of the compound A, and a process for efficiently producing optically active carboxylic acid derivatives from ester derivatives which are useful intermediates of the compound A.

Means for Achieving the Object

The present invention relates to the following (1) to (12).

(1) A process for producing an optically active succinimide derivative represented by the formula (I):

[Formula 3]

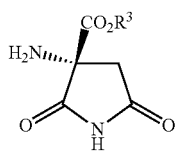

(I)

[in the formula (I), $R^8$ represents a lower alkyl] or a salt thereof, which comprises the following steps (A) to (D), and further comprises the step (E), if necessary:

(A) the step of reacting an aminomalonate derivative represented by the formula (II):

[Formula 4]

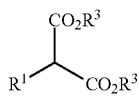

(II)

[in the formula (II), $R^1$ represents amino or an amino protected with a protective group, and two of $R^3$ represent the same lower alkyls having the same meaning as that defined above] and a halogenated acetic acid ester derivative represented by the formula (III):

[Formula 5]

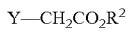

Y—CH$_2$CO$_2$R$^2$ (III)

[in the formula (III), $R^2$ represents a lower alkyl, and Y represents a halogen] in the presence of a base for conversion into an ester derivative represented by the formula (IV):

[Formula 6]

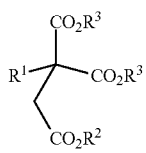

(IV)

[in the formula (IV), each of $R^1$, $R^2$, and $R^3$ has the same meaning as that defined above] or a salt thereof, (B) the step of allowing a non-animal-derived enzyme, a cell that produces the enzyme, a culture of the cell, or a processed product of the cell or a culture of the cell to react on the ester derivative represented by the formula (IV) or a salt thereof to convert the ester or a salt thereof into an optically active carboxylic acid derivative represented by the formula (V):

[Formula 7]

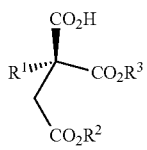

(V)

[in the formula (V), each of $R^1$, $R^2$, and $R^3$ has the same meaning as that defined above] or a salt thereof, (C) the step of reacting the optically active carboxylic acid derivative represented by the formula (V) or a salt thereof with an ammonia source in the presence of a condensing agent, or reacting the optically active carboxylic acid derivative represented by the formula (V) or a salt thereof with an activating reagent and then reacting the resultant with an ammonia source for conversion into an optically active amide derivative represented by the formula (VI):

[Formula 8]

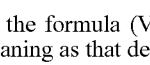

(VI)

[in the formula (VI), each of $R^1$, $R^2$, and $R^3$ has the same meaning as that defined above] or a salt thereof, (D) the step of allowing a base to react on the optically active amide derivative represented by the formula (VI) or a salt thereof for conversion into an optically active succinimide derivative represented by the formula (I) or (VII):

[Formula 9]

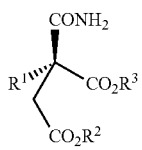

(VII)

[in the formula (VII), $R^{14}$ represents an amino protected with a protective group, and $R^3$ has the same meaning as that defined above] or a salt thereof, and (E) the step of eliminating the protective group on $R^{14}$ of the optically active succinimide derivative represented by the formula (VII) or a salt thereof for conversion into an optically active succinimide derivative represented by the aforementioned formula (I) or a salt thereof.

(2) A process for producing an optically active carboxylic acid derivative represented by the formula (V) or a salt thereof, which comprises the step of allowing a non-animal-derived enzyme, a cell that produces the enzyme, a culture of the cell, or a processed product of the cell or a culture of the cell to react on an ester derivative represented by the formula (IV) or a salt thereof.

(3) The production process according to (1) or (2), wherein the enzyme is an esterase derived from a microorganism.

(4) The production process according to (1) or (2), wherein the enzyme is an esterase derived from a microorganism belonging to the genus *Bacillus*.

(5) The production process according to (1) or (2), wherein the enzyme is an esterase derived from *Bacillus thuringiensis*.
(6) The production process according to (1) or (2), wherein the enzyme is a protein selected from the following (a) to (d):
(a) a protein identified by the amino acid sequence shown in SEQ ID NO: 2,
(b) a protein consisting of an amino acid sequence resulting from substitution, deletion, and/or addition of one or more amino acid residues in the amino acid sequence shown in SEQ ID NO: 2, and having an esterase activity similar to that of the esterase identified by the amino acid sequence shown in SEQ ID NO: 2,
(c) a protein consisting of an amino acid sequence having 95% or more identity to the amino acid sequence shown in SEQ ID NO: 2, and having an esterase activity similar to that of the esterase identified by the amino acid sequence shown in SEQ ID NO: 2,
(d) a protein comprising the amino acid sequence, wherein 1 to 40 amino acid residues from the N-terminus in the amino acid sequence shown in SEQ ID NO: 2 are deleted.
(7) The production process according to any one of (1) to (6), wherein $R^1$ and $R^{1A}$ are benzyloxycarbonylamino groups, $R^2$ is ethyl, and $R^3$ is ethyl.
(8) A process for producing the compound A, which comprises the step of producing an optically active succinimide derivative represented by the formula (I) {henceforth referred to as compound (I)} by the production process according to (1), and the step of converting the compound (I) obtained in the above step into the compound A.
(9) A process for producing the compound A, which comprises the following steps (a) to (e):
(a) the step of producing the compound (I) by the method according to (1);
(b) the step of reacting the compound (I) obtained in the step (a) with 2,5-dimethoxytetrahydrofuran in the presence of an acid (for example, acetic acid and the like);
(c) the step of reacting the product obtained in the step (b) with a trichloroacetylating reagent (for example, trichloroacetyl chloride, trichloroacetyl bromide, trichloroacetic anhydride, and the like);
(d) the step of reacting the product obtained in the step (c) with 4-bromo-2-fluorobenzylamine; and
(e) the step of isolating the compound A obtained in the step (d).
(10) The production process according to (8) or (9), wherein $R^3$ is ethyl.
(11) A protein selected from the following (a) to (d):
(a) a protein identified by the amino acid sequence shown in SEQ ID NO: 2,
(b) a protein consisting of an amino acid sequence resulting from substitution, deletion, and/or addition of one or more amino acid residues in the amino acid sequence shown in SEQ ID NO: 2, and having an esterase activity similar to that of the esterase identified by the amino acid sequence shown in SEQ ID NO: 2,
(c) a protein consisting of an amino acid sequence having 95% or more identity to the amino acid sequence shown in SEQ ID NO: 2, and having an esterase activity similar to that of the esterase identified by the amino acid sequence shown in SEQ ID NO: 2,
(d) a protein comprising the amino acid sequence, wherein 1 to 40 amino acid residues from the N-terminus in the amino acid sequence shown in SEQ ID NO: 2 are deleted.
(12) A DNA selected from the following (a) to (d):
(a) a DNA identified by the nucleotide sequence shown in SEQ ID NO: 1,
(b) a DNA encoding the protein according to (11),
(c) a DNA consisting of a nucleotide sequence resulting from substitution, deletion, and/or addition of one or more nucleotide residues in the nucleotide sequence shown in SEQ ID NO: 1, and encoding a protein having an esterase activity similar to that of the esterase identified by the amino acid sequence shown in SEQ ID NO: 2,
(d) a DNA consisting of a nucleotide sequence that hybridizes with a DNA consisting of a nucleotide sequence complementary to the nucleotide sequence shown in SEQ ID NO: 1 under a stringent condition, and encoding a protein having an esterase activity similar to that of the esterase identified by the amino acid sequence shown in SEQ ID NO: 2.

Effect of the Invention

According to the production process of the present invention, the optically active carboxylic acid derivatives can be efficiently produced from the ester derivatives which are useful intermediates of the compound A. In particular, the compound (I) and the compound A of high optical purity can be produced in a high yield according to the processes of the present invention, and therefore, they are advantageous from an industrial point of view and the like

MODES FOR CARRYING OUT THE INVENTION

It is defined above that the compound represented by the formula (I) is referred to as the compound (I), and such designation scheme is henceforth also applied to the compounds of the other formula numbers.

In the definitions of the groups included in the formulas (I) to (VII):
examples of the lower alkyl include, for example, a linear or branched alkyl having 1 to 6 carbon atoms, more specifically, methyl, ethyl, propyl, isopropyl, butyl, isobutyl, sec-butyl, tert-butyl, pentyl, isopentyl, neopentyl, hexyl, and the like. The halogen means an atom of fluorine, chlorine, bromine, or iodine.

Examples of the protective group of the "amino protected with a protective group" include, for example, protective groups for amino usually used in the organic synthesis chemistry [for example, those described in T. W. Greene, Protective Groups in Organic Synthesis, third edition, John Wiley & Sons Inc. (1999), and the like], and more preferred examples include such protective groups that can be deprotected by an action of a thiol or an acid, hydrogenolysis, or the like.

Examples of the protective group that can be deprotected by an action of a thiol include, for example, 2-nitrobenzenesulfonyl, 4-nitrobenzenesulfonyl, 2,4-dinitrobenzenesulfonyl, and the like.

Examples of the protective group that can be deprotected by an action of an acid include, for example, acetyl, trityl, tert-butoxycarbonyl, and the like, and more preferred examples include tert-butoxycarbonyl.

Examples of the protective group that can be deprotected by hydrogenolysis include, for example, benzyloxycarbonyl, benzyl and the like, which may have 1 to 3 substituents selected from the group consisting of a halogen atom, lower alkyl, lower alkoxyl and nitro on the benzene ring. More preferred examples include benzyloxycarbonyl, 4-nitrobenzyloxycarbonyl, 4-chlorobenzyloxycarbonyl, 4-methylbenzyloxycarbonyl, 2-methoxybenzyloxycarbonyl, benzyl, 4-nitrobenzyl, 4-chlorobenzyl, 4-methylbenzyl, 2-methoxybenzyl, 4-methoxybenzyl, and the like.

In the present invention, the amino protected with a protective group may be converted into amino during the reaction.

Examples of $R^1$ and $R^{1A}$ in the formulas include, for example, an amino protected with a protective group that can be deprotected by an action of a thiol or an acid, or hydrogenolysis, and the like, and preferred examples include benzyloxycarbonylamino and tert-butoxycarbonylamino.

Examples of $R^2$ and $R^3$ in the formulas include, for example, ethyl, and the like.

Examples of preferred combination of $R^1$, $R^2$ and $R^3$ include, for example, such a combination that $R^1$ is benzyloxycarbonylamino, and $R^2$ and $R^3$ are ethyl groups. Examples of preferred combination of $R^{1A}$ and $R^3$ include, for example, such a combination that $R^{1A}$ is benzyloxycarbonylamino and $R^3$ is ethyl.

Examples of Y include a halogen, and preferred examples include iodine, bromine, chlorine, and the like. More preferred examples include bromine and chlorine.

Examples of the ammonia source include ammonia, an ammonia equivalent, and the like, and preferred examples include ammonia. Examples of the form of ammonia include gas or aqueous solution, and preferred examples include aqueous solution.

Examples of the ammonia equivalent include, for example, a salt of ammonia and an acid, preferred examples include ammonium acetate, ammonium formate, and ammonium carbonate, and more preferred examples include ammonium acetate.

Examples of the condensing agent include, for example, dicyclohexylcarbodiimide (DCC), 1-ethyl-3-(3-dimethylaminopropyl)-carbodiimide hydrochloride, N,N'-carbonyldiimidazole (CDI), N-hydroxybenzotriazole (HOBT), diphenylphosphoric acid azide (DPPA), N-hydroxysuccinimide, N-hydroxyphthalimide, benzotriazol-1-yloxytrisdimethylaminophosphonium hexafluorophosphate (BOP), 4-(4,6-dimethoxy-1,3,5-triazin-2-yl)-4-methylmorpholinium chloride (DMTMM), O-(benzotriazol-1-yl)-N,N,N',N'-tetramethyluronium hexafluorophosphate (HBTU), 2-chloro-1-methylpyridinium iodide, and the like.

Examples of the activating reagent include, for example, methyl chloroformate, ethyl chloroformate, isopropyl chloroformate, isobutyl chloroformate, pivaloyl chloride, phosgene, triphosgene, phosphorus oxychloride, phosphorus pentachloride, thionyl chloride, and the like, and preferred examples include isobutyl chloroformate.

Examples of the salt of the compound (I), (IV), (V), (VI) or (VII) include, for example, an acid addition salt, metal salt, ammonium salt, organic amine addition salt, amino acid addition salt, and the like. Examples of the acid addition salt include, for example, an inorganic acid salt such as hydrochloride, hydrobromide, nitrate, sulfate, and phosphate, organic acid salt such as acetate, oxalate, maleate, fumarate, citrate, benzoate and methanesulfonate, and the like. Examples of the metal salt include, for example, an alkali metal salt such as sodium salt and potassium salt, alkaline earth metal salt such as magnesium salt and calcium salt, aluminum salt, zinc salt, and the like. Examples of the ammonium salt include, for example, salts of ammonium, tetramethylammonium, and the like, and examples of the organic amine addition salt include addition salts of morpholine, piperidine, and the like Examples of the amino acid addition salt include, for example, addition salts of lysine, glycine, phenylalanine, aspartic acid, glutamic acid, and the like.

The production process of the present invention is characterized by the use of a non-animal-derived esterase, preferably an esterase derived from a microorganism, more preferably an esterase derived from a microorganism belonging to the genus Bacillus, most preferably an esterase derived from Bacillus thuringiensis, in the "step 2" among the steps described below.

The production processes of the present invention will be explained below. However, the reaction conditions such as reaction temperatures, types of reagents, amounts of reagents and reaction times are mentioned merely for exemplification, and they should not be construed any limitative way.

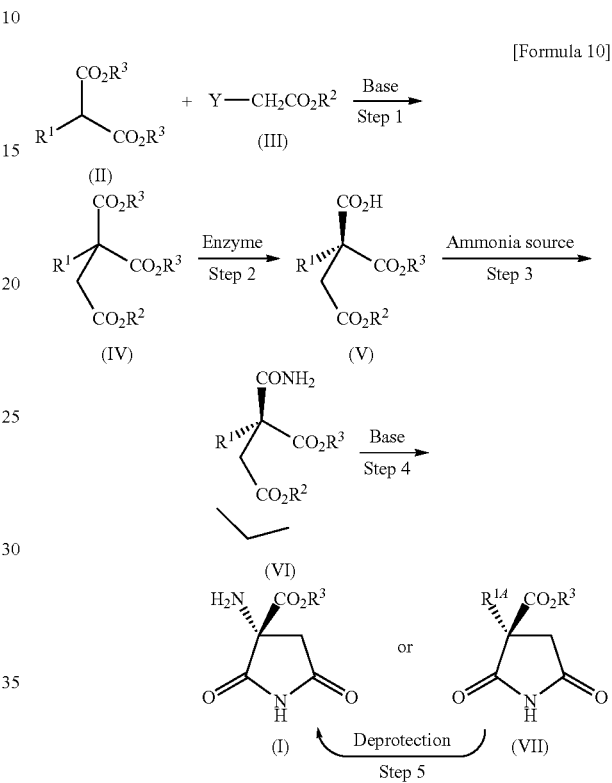

[Formula 10]

(In the formulas, $R^1$ represents amino or an amino protected with a protective group, $R^{1A}$ represents an amino protected with a protective group, $R^2$ and $R^3$ are the same or different, and represent a lower alkyl, and Y represents halogen.)

(Step 1)

By reacting one equivalent to a large excess amount of the compound (III) with the compound (II) in a solvent at a temperature of −50 to 150° C. for 5 minutes to 72 hours in the presence of 1 to 30 equivalents of a base, the compound (IV) can be obtained. The reaction may be performed with addition of an alkali halide.

As the solvent, any solvent that does not participate in the reaction may be used. Examples include cyclohexane, benzene, toluene, xylene, diethyl ether, diisopropyl ether, tert-butyl methyl ether, tetrahydrofuran (THF), dioxane, pyridine, methanol, ethanol, isopropyl alcohol, dimethylformamide (DMF), dimethyl sulfoxide (DMSO), acetonitrile, and the like, and preferred examples include DMF. These can be used independently or as a mixture.

Examples of the base include an organic base and an inorganic base, preferred examples include an inorganic base, more preferred examples include sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like, still more preferred examples include sodium hydride, sodium carbonate, sodium hydrogencarbonate, potassium carbonate, potassium hydrogencarbonate, cesium carbonate, and the like, and most preferred examples include sodium hydride and potassium carbonate.

Examples of the alkali halide include an alkali bromide, an alkali iodide, and the like, preferred examples include an alkali iodide, and more preferred examples include lithium iodide, sodium iodide, potassium iodide, and cesium iodide. Most preferred examples include potassium iodide.

Examples of the compound (III) include ethyl 2-chloroacetate, ethyl 2-bromoacetate, and the like.

The compound (II) and the compound (III) can also be obtained as marketed products.

(Step 2)

By allowing an enzyme in an amount of 1/100,000 to 10-fold, preferably 1/10,000 to 1-fold, based on the substrate to react on the compound (IV) in water or a mixed solvent of water and a solvent at a substrate concentration of 0.1 to 50%, preferably 1 to 30%, a temperature of 0 to 60° C., preferably 10 to 40° C., and a reaction pH of 3 to 10, preferably 4 to 9, to allow the reaction for 1 to 200 hours, preferably 5 to 150 hours, the compound (V) can be obtained. The reaction can also be performed with adding a buffer or a metal salt.

Examples of the solvent include cyclohexane, benzene, toluene, xylene, diethyl ether, diisopropyl ether, tert-butyl methyl ether, THF, dioxane, methyl acetate, ethyl acetate, butyl acetate, methyl isobutyl ketone, acetone, dichloromethane, chloroform, dichloroethane, carbon tetrachloride, methanol, ethanol, isopropyl alcohol, tert-butyl alcohol, DMF, DMSO, acetonitrile, and the like, and preferred examples include ethanol and acetonitrile. When a mixed solvent is used, the solvent may form a homogeneous system or a heterogeneous system of water and a solvent, and the solvent preferably forms such a homogeneous system.

Examples of the enzyme include a non-animal-derived esterase, preferably an esterase derived from a microorganism. As the microorganism, for example, a microorganism belonging to the genus *Bacillus* is preferred. Examples of the microorganism belonging to the genus *Bacillus* include, for example, *Bacillus thuringiensis, Bacillus subtilis, Bacillus anthracis, Bacillus cereus, Bacillus coagulans, Bacillus licheniformis, Bacillus megaterium, Bacillus stearothermophilus, Bacillus amyloliquefaciens, Bacillus pumilus*, and the like, but it is not limited to these. An esterase derived from *Bacillus thuringiensis* is preferred, but it is not limited to the aforementioned specific esterase.

Examples of the esterase derived from *Bacillus thuringiensis* include, for example, an esterase consisting of the amino acid sequence shown in SEQ ID NO: 2. For the method of the present invention, as well as the aforementioned specific esterase, a protein consisting of an amino acid sequence having 95% or more, preferably 97% or more, more preferably 99% or more identity to the amino acid sequence mentioned above, and having an esterase activity similar to that of the aforementioned esterase can also be used. Examples further include a protein encoded by a DNA consisting of the nucleotide sequence shown in SEQ ID NO: 1, a protein encoded by a DNA consisting of a nucleotide sequence having 95% or more, preferably 97% or more, more preferably 99% or more identity to the nucleotide sequence mentioned above, and having an esterase activity similar to that of the aforementioned esterase, and the like.

When an esterase derived from a microorganism is used as the esterase, cells of the microorganism separated from culture of the microorganism, culture of the microorganism, or a processed product of the cells, or a processed product of the culture of the microorganism obtainable by subjecting separated cells of the microorganism or culture of the microorganism to an appropriate treatment may also be used. It should be understood that an embodiment of using cells of the microorganism, culture, processed product of the cells or culture or the like containing an esterase also falls within embodiments of using an esterase derived from a microorganism. Examples of the processed product of cells or culture include, for example, lyophilized products of cells or culture, and cell processed products obtained by a treatment with toluene, acetone or the like, as well as immobilized products obtained by immobilizing cells by a known immobilization method such as the entrapment method, carrier binding method, and cross-linking method, and the like. Examples of the entrapment method include methods utilizing a natural polymer such as carrageenan and alginic acid, or a synthetic polymer produced from monomers or prepolymers, examples of the carrier binding method include methods utilizing chitosan or the like for adsorbing the enzyme, and examples of the cross-linking method include methods utilizing glutaraldehyde or the like.

Further, a disruption product or extract of cells may also be used as the cell processed product. The disruption product of cells can be obtained by a known cell disruption method, for example, disruption with ultrasonication, French press, glass beads, dyno-mill, or the like. An extract of cells can be obtained from a cell disruption product by removing the cells by centrifugation or the like. Although an extract of cells can be used as a crude enzyme solution, such a crude enzyme solution can also be purified by a combination of, for example, salting-out based on ammonium sulfate precipitation, concentration using an ultrafiltration membrane, ion exchange chromatography, hydrophobic interaction chromatography, gel filtration chromatography, and the like, and used as a purified enzyme. In this specification, the term of cell processed product includes such disrupted cell product, cell extract, crude enzyme solution, and purified enzyme as mentioned above.

If a cell disruption product or extract (crude enzyme or purified enzyme) as the cell processed product is immobilized on a carrier, the immobilized cells or immobilized enzyme can be repeatedly used. By using immobilized cells or immobilized enzyme, the objective substance can also be produced by a continuous method, and for example, it can be filled in a column, and used as a bioreactor. As the carrier, any of generally used carriers may be used. Examples include, for example, polysaccharides such as cellulose, agarose, dextran, κ-carrageenan, alginic acid, gelatin, and cellulose acetate, natural polymers such as gluten, inorganic substances such as activated charcoal, glass, white clay, kaolinite, alumina, silica gel, bentonite, hydroxyapatite, and calcium phosphate, synthetic adsorbents such as polyacrylamide, polyvinyl acetate, polypropylene glycol, and urethane, and the like. As the immobilization method, for example, the cross-linking method, physical adsorption method, and entrapment method can be used.

Culture conditions of the microorganism are not particularly limited, and the culture can be performed according to an ordinarily used method. The medium may be an ordinarily used medium, and any medium can be used so far that the medium allows growth of microorganisms and appropriately contains assimilable carbon source, nitrogen source, inorganic substances, and required growth-promoting substances. As the medium, either a synthetic medium or a natural medium may be used.

As the carbon source, any of carbon compounds that can be assimilated by the cells to allow growth thereof can be used. For example, saccharides such as glucose, fructose, maltose, sucrose, dextrin, soluble starch, gelatinized starch and sorbitol, alcohols such as methanol, ethanol and glycerol, organic acids such as fumaric acid, citric acid, acetic acid and propionic acid, and salts of these, hydrocarbons such as paraffin, molasses, rape seed oil, and the like can be used alone or as a mixture thereof.

As the nitrogen source, ammonium salts of inorganic acid such as hydrochloric acid, sulfuric acid, nitric acid, and phosphoric acid, ammonium salts of organic acids such as fumaric acid and citric acid, nitric acid salts such as sodium nitrate and potassium nitrate, and organic nitrogen sources such as yeast extract, peptone, meat extract, corn steep liquor, soybean processed product and urea can be used alone or as a mixture thereof.

As the inorganic salts, sulfates, hydrochlorides, carbonates, nitrates, phosphates, and the like of potassium, sodium, calcium, magnesium, manganese, iron, and the like can used alone or as a mixture thereof. Furthermore, nutrients used for usual culture such as vitamins may be optionally added.

Culture can be performed under an aerated condition as shaking culture or by using a jar fermenter or the like, or under an anaerobic condition depending on type of the microorganism. pH of the medium is preferably in the range of 3 to 10, temperature is preferably in the range of 10 to 50° C., and a period of time for culture is preferably in the range of 10 to 500 hours. However, such culture conditions as mentioned above can be appropriately chosen according to type of the microorganism, and are not limited to the aforementioned specific conditions.

In another embodiment, for example, a recombinant vector can be prepared which contains a DNA comprising the nucleotide sequence identified by SEQ ID NO: 1, or contains a DNA consisting of a nucleotide sequence having 95% or more, preferably 97% or more, more preferably 99% or more identity to the nucleotide sequence mentioned above, and encoding a protein having an esterase activity similar to that of the esterase of SEQ ID NO: 2, and then the resulting vector can be introduced into an appropriate host cell to prepare a transformant and thereby obtain the protein encoded by the DNA, and the resulting protein can be used as the esterase. A DNA that hybridizes with a DNA specified by the nucleotide sequence shown in SEQ ID NO: 1 under a stringent condition, or a DNA comprising a nucleotide sequence resulting from substitution, deletion, and/or addition of one or more nucleotide residues, preferably 1 to 120 nucleotide residues, more preferably 1 to several tens of nucleotide residues, still more preferably one to several nucleotide residues in the nucleotide sequence shown in SEQ ID NO: 1 may also be used. As already explained, when the aforementioned transformant is a microorganism, a cell processed product or the like obtainable by subjecting culture of the microorganism or separated cells of the microorganism to an appropriate treatment may also be used, as well as the microorganism.

The term "hybridize" used in this specification refers to a process of hybridization of a DNA to another DNA having a specific nucleotide sequence, or a part of that DNA. Therefore, the nucleotide sequence of the DNA having a specific nucleotide sequence, or the part of that DNA may be a DNA having such a length that it is useful as a probe for Northern or Southern blot analysis, or it may be used as an oligonucleotide primer for PCR analysis. A DNA used as such a probe may be a DNA having, for example, at least 100 or more nucleotides, preferably 200 or more nucleotides, more preferably 500 or more nucleotides, and it may also be DNA having at least 10 or more nucleotides, preferably 15 or more nucleotides.

Methods for hybridization experiment of DNA are well known, and the hybridization conditions can be determined according to the descriptions of, for example, Molecular Cloning, 2nd edition and 3rd edition (2001), Methods for General and Molecular Bacteriology, ASM Press (1994), Immunology methods manual, Academic press (Molecular), and many other standard textbooks to perform experiments.

Examples of the aforementioned stringent condition include, for example, a condition that a filter on which DNA is immobilized and a probe DNA are incubated overnight at 42° C. in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/l of denatured salmon sperm DNA, and then the filter is washed in a 0.2×SSC solution at about 65° C. A lower stringency condition can also be used. The stringent condition can be changed by altering concentration of formamide (lower concentration of formamide affords lower stringency), salt concentrations, and temperature condition. Examples of lower stringency condition include, for example, a condition that the incubation is performed at 37° C. overnight in a solution containing 6×SSCE (20×SSCE corresponds to 3 mol/l of sodium chloride, 0.2 mol/l of sodium dihydrogenphosphate, 0.02 mold of EDTA, pH 7.4), 0.5% SDS, 30% formamide, and 100 µg/1 of denatured salmon sperm DNA, and then the washing is performed with a solution containing 1×SSC and 0.1% SDS at 50° C. Further, examples of further lower stringent condition include a condition that the hybridization is performed under the aforementioned low stringent condition using a solution of a high salt concentration (e.g., 5×SSC), and then the washing is performed.

The aforementioned various conditions can also be set by adding or changing the blocking reagent used for suppressing the background of the hybridization experiment. When the aforementioned blocking reagent is added, the hybridization conditions may also be changed in order to adjust the conditions.

Examples of DNA that can hybridize under the aforementioned stringent condition include a DNA consisting of a nucleotide sequence having 95% or more, preferably 97% or more, more preferably 99% or more identity to the nucleotide sequence shown in SEQ ID NO: 1, as calculated by using a program such as BLAST and FASTA.

Whether a DNA that hybridizes with the aforementioned DNA under a stringent condition is a DNA encoding a protein having an esterase action similar to that of the esterase of SEQ ID NO: 2 can be conformed by preparing a recombinant DNA that expresses the DNA, introducing the recombinant DNA into a host cell, culturing the resulting microorganism, preparing a crude enzyme extract or the like from the resulting culture, reacting the enzyme with a compound (IV), and confirming whether or not a compound (V) is generated.

A DNA encoding a protein consisting of an amino acid sequence resulting from substitution, deletion, and/or addition of one or more amino acid residues, preferably 1 to 40, more preferably 1 to 30, still more preferably 1 to several amino acid residues in the amino acid sequence shown in SEQ ID NO: 2, and having an esterase activity similar to that of the esterase specified by the amino acid sequence shown in SEQ ID NO: 2 can be prepared by an arbitrary method known to those skilled in the art, such as chemical synthesis, genetic engineering technique, or mutagenesis, on the basis of the information on the amino acid sequence shown in SEQ ID NO: 2. For example, by using a DNA comprising a nucleotide sequence encoding the amino acid sequence shown in SEQ ID NO: 2 in Sequence Listing, for example, a DNA comprising the nucleotide sequence shown in SEQ ID NO: 1, a desired DNA can be prepared by a method of contacting the DNA with an agent serving as a mutagen, a method of irradiating ultraviolet radiation, a genetic engineering technique, or the like. The site-directed mutagenesis method, as one of genetic engineering techniques, is a method capable of introducing a specific mutation at a specific position, and it can be performed according to, for example, the method described in Molecular Cloning, 2nd edition, "Current Protocols in Molecular Biology", John Wiley & Sons (1987-1997).

Further, a protein consisting of an amino acid sequence having 95% or more, preferably 97% or more, more preferably 99% or more identity to the amino acid sequence shown in SEQ ID NO: 2, and having an esterase activity similar to that of the esterase specified by the amino acid sequence shown in SEQ ID NO: 2 can be prepared by obtaining an amino acid sequence having 95% or more identity to the aforementioned amino acid sequence through searching of various databases of proteins using the amino acid sequence shown in SEQ ID NO: 2 as a query, expressing an enzyme having the resulting amino acid sequence using a recombinant DNA as described above, and confirming the activity of the enzyme.

Further, the aforementioned DNA can also be obtained by preparing an appropriate probe or primer on the basis of the information on the amino acid sequence shown in SEQ ID NO: 2 in Sequence Listing, and screening chromosomes of microorganisms by using the probe or primer. For example, a desired DNA can be isolated by the PCR method using a chromosomal DNA library derived from any of various microorganisms or a cDNA library as a template. Methods for preparation of the aforementioned probe or primer, construction of cDNA library, screening of a cDNA library, cloning of an objective DNA, and the like are well known to and conventionally used by those skilled in the art, and can be performed according to, for example, the methods described in "Current Protocols in Molecular Biology" mentioned above, and the like.

For used of a DNA comprising the nucleotide sequence identified by SEQ ID NO: 1, or a DNA consisting of a nucleotide sequence having 95% or more, preferably 97% or more, more preferably 99% or more identity to the aforementioned nucleotide sequence, and encoding a protein having an esterase activity similar to that of the esterase of SEQ ID NO: 2, the DNA can be inserted into an appropriate vector. Type of the vector used for the present invention is not particularly limited, and for example, an autonomously replicable vector such as plasmids, a vector that is incorporated into a genome of a host cell when it is introduced into the host cell, and replicated together with the chromosome, and the like can be used. It is preferable to use an expression vector for expressing a desired protein from the aforementioned DNA, and in such an expression vector, the aforementioned DNA is preferably functionally ligated with a promoter or the like required for transcription. Promoter is a DNA sequence having a transcription activity in a host cell, and can be appropriately chosen according to type of the host.

Examples of promoter that can function in bacterial cells include, for example, promoters of *Bacillus stearothermophilus* maltogenic amylase gene, *Bacillus licheniformis* α-amylase gene, *Bacillus amyloliquefaciens* BAN amylase gene, *Bacillus Subtilis* alkaline protease gene, and *Bacillus pumilus* xylosidase gene, $P_R$ and $P_L$ promoters of lambda phage, lac, trp, and tac promoters of *Escherichia coli*, and the like. Example of promoter that can function in insect cells include the polyhedrin promoter, P10 promoter, *Autographa californica* polyhedrosis basic protein promoter, baculovirus immediate early gene 1 promoter, baculovirus 39K delayed early gene promoter, and the like. Examples of promoter that can function in yeast host cells include a promoter derived from a yeast glycolysis gene, alcohol dehydrogenase gene promoter, TPI1 promoter, ADH2-4c promoter, and the like. Examples of promoter that can function in filamentous fungi include ADH3 promoter, tpiA promoter, and the like.

The recombinant vector may further comprise a selection marker. Examples of the selection marker include, for example, a drug resistance gene such as drug resistance genes for ampicillin, kanamycin, tetracycline, chloramphenicol, neomycin, or hygromycin. Methods for ligating the aforementioned DNA, and promoter, as well as terminator and/or secretion signal sequence, and the like as required in an appropriate order, and inserting them into an appropriate vector are well known to those skilled in the art.

Type of the host cell to which the recombinant vector is introduced is not particularly limited, so far that the host cell can express the aforementioned DNA. Examples include, for example, bacteria, yeasts, fungi, higher eucaryocytes, and the like, and bacteria, yeasts, and the like are preferred. Examples of the bacteria include gram-positive bacteria belonging to the genus *Bacillus, Streptomyces*, or the like, and gram-negative bacteria such as *Escherichia coli*, and *Escherichia coli* and the like are preferred. These bacteria can be transformed by using an appropriate means according to type of the cell. By culturing a transformant under appropriate conditions, an esterase can be expressed from the introduced DNA, and then the esterase can be isolated, purified with appropriate means, and used for the method of the present invention. As previously explained, when a microorganism is used as the transformant, it is also possible to use the cell, per se, a cell processed product, or the like. For example, the aforementioned DNA can be introduced into a plasmid to prepare a recombinant vector, this recombinant vector can be introduced into *Escherichia coli* to transform the cell, and then a desired esterase can be obtained by culturing the *Escherichia coli*. However, mode for the use of the transformant is not limited to this specific mode.

Examples of the buffer used for the reaction in the step 2 include, for example, phosphate buffer, acetate buffer, citrate buffer, borate buffer, Tris buffer, and the like, and preferred examples include phosphate buffer. Concentration of the buffer is 0.1 mmol/L to 1 mol/L, preferably 1 mmol/L to 100 mmol/L. Examples of the metal salt include NaCl, $FeCl_3$, KCl, $CaCl_2$, $MgSO_4$, $MnSO_4$, $ZnCl_2$, $CoCl_2$, and the like. Concentration of the metal salt is preferably 0.01 to 10%.

The optically active carboxylic acid derivative of the formula (V) obtained by the aforementioned reaction can be separated by, after completion of the reaction, filtering the reaction mixture to remove insoluble matter, adding an acid to adjust the filtrate to pH 1 to 3, preferably about pH 2, and then extracting the reaction product with an appropriate solvent.
(Step 3)

(A) By reacting one equivalent to a large excess amount of a condensing agent with the compound (V) in a solvent at a temperature of −50 to 150° C., preferably −30 to 80° C., for 5 minutes to 72 hours, then adding one equivalent to a large excess amount of an ammonia source and allowing to react at a temperature of −50 to 150° C., preferably −30 to 80° C., for 5 minutes to 72 hours, (B) by reacting one equivalent to a large excess amount of an activating reagent with the compound (V) in a solvent at a temperature of −50 to 150° C., preferably −30 to 80° C., for 5 minutes to 72 hours, then adding one equivalent to a large excess amount of an ammonia source and allowing to react at a temperature of −50 to 150° C., preferably −30 to 80° C., for 5 minutes to 72 hours, or (C) by adding one equivalent to a large excess amount of an ammonia source to the compound (V) in a solvent at a temperature of −50 to 150° C., preferably 20 to 80° C., in the presence of one equivalent to a large excess amount of a condensing agent and allowing to react for 5 minutes to 72 hours, the compound (VI) can be obtained.

For all the cases of (A) to (C), any solvent that does not participate in the reaction may be used. Examples include, for example, cyclohexane, benzene, toluene, xylene, diethyl ether, diisopropyl ether, tert-butyl methyl ether, THF, dioxane, methyl acetate, ethyl acetate, butyl acetate, methyl isobutyl ketone, acetone, pyridine, DMF, DMSO, dichloromethane, chloroform, acetonitrile, and the like, and preferred examples include THF. These solvents can be used independently or as an arbitrary mixture.

For all the cases of (A) to (C), at the time of the reaction with the ammonia source, such a solvent as water, methanol, ethanol and isopropyl alcohol may be used, in addition to the aforementioned solvent, and these solvents may be used independently or as an arbitrary mixture.

For all the cases of (A) to (C), the reaction may also be performed by adding 1/10 to 30 equivalents of a base.

Examples of the base include an organic base and an inorganic base, and preferred examples include an organic base. Examples of the organic base include, for example 1,8-diazabicyclo[5,4,0]-7-undecene (DBU), triethylamine, 4-dimethylaminopyridine, N,N-dimethylaniline, pyridine, N-methylmorpholine, ethyldiisopropylamine, and the like, and preferred examples include triethylamine. Examples of the inorganic base include, for example, sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like. As the condensing agent, those condensing agents mentioned above can be similarly used. Also as the activation reagent and the ammonia source, those mentioned above can be similarly used.

(Step 4)

By allowing one equivalent to a large excess amount of a base to react on the compound (VI) in a solvent at a temperature of −50 to 150° C., preferably −20 to 60° C., for 5 minutes to 72 hours, the compound (I) or the compound (VII) can be obtained.

Examples of the solvent include cyclohexane, benzene, toluene, xylene, pyridine, diethyl ether, diisopropyl ether, tert-butyl methyl ether, THF, dioxane, water, isopropyl alcohol, methanol, ethanol, DMF, DMSO, and the like, and preferred examples include ethanol. These solvents can be used independently or as an arbitrary mixture.

Examples of the base include sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like, and preferred examples include sodium ethoxide.

(Step 5)

When $R^{14}$ of the compound (VII) is an amino protected with a protective group that can be deprotected by hydrogenolysis, by adding a metal catalyst in an amount of 1/10 to 50% by weight, preferably 1 to 10% by weight, of the substrate in a solvent, and allowing to react at a temperature of −50 to 150° C., preferably 20 to 100° C., under a pressure of 1 to 10 atmospheres, preferably 1 to 5 atmospheres, for 5 minutes to 72 hours in the presence of hydrogen or a hydrogen donor, the compound (I) can be obtained.

Examples of the solvent include acetic acid, methyl acetate, ethyl acetate, butyl acetate, diethyl ether, diisopropyl ether, tert-butyl methyl ether, THF, dioxane, water, methanol, ethanol, isopropyl alcohol, DMF, and the like, and preferred examples include ethanol. These solvents can be used independently or as an arbitrary mixture.

Examples of the metal catalyst include platinum(IV) oxide, platinum/carbon, palladium(II) hydroxide, palladium (II) hydroxide/carbon, palladium/carbon, palladium/alumina, ruthenium/carbon, rhodium/carbon, rhodium/alumina, Wilkinson catalyst, Raney nickel, and the like, and preferred examples include palladium/carbon. Although palladium content in palladium/carbon is not particularly limited, it is preferably, for example, 5 to 10%.

Examples of the hydrogen donor include ammonium formate, cyclohexene, cyclohexa-1,3-diene, cyclohexa-1,4-diene, and the like.

When $R^{14}$ of the compound (VII) is an amino protected with a protective group that can be deprotected by an action of an acid, by allowing an acid to react on the protective group without solvent or in a solvent at a temperature of −50 to 150° C., preferably 20 to 100° C., the compound (I) can be obtained.

Examples of the solvent include cyclohexane, benzene, toluene, xylene, diethyl ether, diisopropyl ether, tert-butyl methyl ether, THF, dioxane, methyl acetate, ethyl acetate, butyl acetate, water, isopropyl alcohol, methanol, ethanol, DMF, dichloromethane, chloroform, and the like, and these solvent can be used independently or as an arbitrary mixture.

Examples of the acid include an inorganic acid, an organic acid, and the like, examples of the inorganic acid include hydrochloric acid, sulfuric acid, nitric acid, and the like, and examples of the organic acid include acetic acid, trifluoromethanesulfonic acid, trifluoroacetic acid, p-toluenesulfonic acid, and the like. Preferred examples include trifluoroacetic acid.

When $R^{14}$ of the compound (VII) is an amino protected with a protective group that can be deprotected by an action of a thiol, by allowing one equivalent to a large excess amount of a thiol to react on the protective group in a solvent at a temperature of −50 to 150° C., preferably 20 to 100° C., for 5 minutes to 72 hours in the presence of one equivalent to a large excess amount of a base, the compound (I) can be obtained.

Examples of the solvent include cyclohexane, benzene, toluene, xylene, pyridine, diethyl ether, THF, dioxane, methyl acetate, ethyl acetate, butyl acetate, water, acetone, isopropyl alcohol, methanol, ethanol, DMF, dichloromethane, chloroform, and the like, and these solvent can be used independently or as an arbitrary mixture.

As the thiol, any compound having sulfhydryl group can be used. Preferred examples include a thiophenol which may have a substituent and a lower alkyl thiol which may have a substituent, and more preferred examples include thiophenol, methanethiol, ethanethiol, 1-dodecanethiol, and the like.

Examples of the base include an organic base and an inorganic base. Examples of the organic base include, for example, DBU, triethylamine, 4-dimethylaminopyridine, N,N-dimethylaniline, pyridine, N-methylmorpholine, ethyldiisopropylamine, and the like, and examples of the inorganic base include, for example, sodium hydride, sodium hydroxide, potassium hydroxide, sodium carbonate, sodium hydrogencarbonate, potassium carbonate, potassium hydrogencarbonate, sodium methoxide, sodium ethoxide, potassium tert-butoxide, and the like, and preferred examples include potassium carbonate and triethylamine.

It is described in Non-patent document 3 that the compound (I) and the compound B:

[Formula 11]

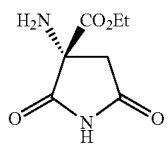

(Compound B)

can be used as intermediates of the compound A, and accordingly, it is obvious to those skilled in the art that the compound (I) and the compound B can be used as raw materials for the production of compound A. According to the descriptions of the above literature, for example, each of the steps (b) to (e) of (9) mentioned above are performed as follows.

In the step (b), for example, a mixture of the compound B, about 1.5 equivalents of 2,5-dimethoxytetrahydrofuran and an excess amount of acetic acid is stirred at about 70° C. for about 1.5 hours. In a usual case, a crude reaction product can be isolated in a conventional manner, and this product can be used for the following step.

In the step (c), for example, a mixture of the product obtained in the aforementioned step (b), about 3 equivalents of trichloroacetyl chloride and an appropriate amount of chloroform is refluxed by heating for about 16 hours. Instead of chloroform, another inert solvent (for example, dichloromethane, THF, and the like) can also be used. In a usual case, a crude reaction product can be isolated in a conventional manner, and this product can be used for the following step.

In the step (d), for example, the product obtained in the aforementioned step (c), about 1.2 equivalents of 4-bromo-2-fluorobenzylamine hydrochloride, and about 2.5 equivalents of triethylamine are stirred at room temperature for about 16 hours in an appropriate amount of dry DMF solvent. In a usual case, a crude reaction product (the compound A) can be isolated in a conventional manner, and this product can be used for the following step.

In the step (e), for example, the compound A obtained in the step (d) is recrystallized from an appropriate amount of a mixed solvent of ethyl acetate and hexane. As other recrystallization solvents, alcohols such as ethanol can also be used.

EXAMPLES

Hereafter, the present invention will be more specifically explained with reference to examples and reference examples. However, the present invention is not limited to these examples.

The proton nuclear magnetic resonance ($^1$H NMR) spectra mentioned in the examples and the reference examples were measured at 300 MHz, and depending on the type of compound and measurement conditions, exchangeable proton may not be clearly observed. As indications of the multiplicity of signals, those usually used are applied, and "br" indicates a signal having an apparently large width. Furthermore, molecular weights of the compounds were confirmed by mass spectrometry (MS).

As for the conversion reaction from diethyl 2-benzyloxycarbonylamino-2-ethoxycarbonylsuccinate to (R)-1-ethyl hydrogen 3-benzyloxycarbonylamino-3-ethoxycarbonylsuccinate, content analysis was performed, and production amount was obtained as volume×content, and used to calculate the yield. The content analysis was performed by HPLC under the following conditions. More specifically, the column was Inertsil ODS-3 (φ4.6×75 mm, 3 μm) produced by GL Sciences Inc., the developing solvent was acetonitrile/0.05 mol/L phosphate buffer (pH 2.5)=50/50 (volume ratio), the flow rate was 1.0 mL/minute, the oven temperature was 40° C., and the detection wavelength was 254 nm. The content was determined by using a calibration curve prepared with standard solutions of known concentrations.

The optical purity analysis was performed by HPLC under the following conditions. As the column, CHIRALCEL OJ-RH (φ4.6×150 mm) produced by Daicel Chemical Industries, Ltd. was used. The optical purity analysis of 1-ethyl hydrogen 3-benzyloxycarbonylamino-3-ethoxycarbonylsuccinate was performed with acetonitrile/aqueous perchloric acid (pH 2.0)=30/70 (volume ratio) as the developing solvent at a flow rate of 1.0 mL/minute, oven temperature of 20° C., and detection wavelength of 254 nm. The optical purity analysis of diethyl 2-benzyloxycarbonylamino-2-carbamoylsuccinate was performed with acetonitrile/water=30/70 (volume ratio) as the developing solvent at a flow rate of 0.5 mL/minute, oven temperature of 20° C., and detection wavelength of 254 nm. The optical purity analysis of 2-benzyloxycarbonylamino-2-ethoxycarbonylsuccinimide was performed with acetonitrile/aqueous perchloric acid (pH 2.0)=30/70 (volume ratio) as the developing solvent at a flow rate of 0.5 mL/minute, oven temperature of 20° C., and detection wavelength of 254 nm. The optical purity analysis of (R)-2-amino-2-ethoxycarbonylsuccinimide was performed with aqueous perchloric acid (pH 1.0) as the developing solvent at a flow rate of 0.45 mL/minute, oven temperature of 5° C., and detection wavelength of 196 nm.

The intermediates and the objective compounds in the aforementioned production processes can be isolated and purified with separation and purification methods usually used in the synthetic organic chemistry, for example, filtration, extraction, washing, drying, concentration, recrystallization, various chromatography techniques, and the like. The intermediates may also be used for the subsequent reactions without particular purification.

In case a salt of the compound (I), (IV), (V), (VI) or (VII) is desired to be obtained, when the compound (I), (IV), (V), (VI) or (VII) is obtained in the form of salt, the salt per se may be purified, and when the compound (I), (IV), (V), (VI) or (VII) is obtained in a free form, the compound can be dissolved or suspended in an appropriate solvent, an acid or a base can be added to the solution or suspension, and a resulted salt can be separated and purified.

The compound (I), (IV), (V), (VI) or (VII), and a salt thereof may exist in the form of adduct with water or various solvents, and such adducts also fall within the scope of the present invention.

Example 1

Production of diethyl 2-benzyloxycarbonylamino-2-ethoxycarbonylsuccinate (Ethyl chloroacetate method)

A suspension of diethyl 2-benzyloxycarbonylaminomalonate (5.0 g), potassium carbonate (2.7 g), potassium iodide (0.27 g), and ethyl 2-chloroacetate (2.6 g) in DMF (50 mL) was stirred at 50° C. for 1 hour. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was crystallized from ethyl acetate/n-hexane to obtain the title compound (5.5 g, yield: 86%) as colorless crystals.

$^1$H NMR (CDCl$_3$) δ (ppm): 7.34 (5H, m), 6.39 (1H, s), 5.10 (2H, s), 4.24 (4H, q, J=6.9 Hz), 4.10 (2H, q, J=7.2 Hz), 3.49 (2H, s), 1.21 (9H, m)

MS (FAB): m/z 396 (M+H$^+$)

HR-MS (FAB): calcd for C$_{19}$H$_{26}$NO$_8$ 396.1658, found 396.1653 (M+H$^+$)

Example 2

Production of diethyl 2-benzyloxycarbonylamino-2-ethoxycarbonylsuccinate (Ethyl bromoacetate method)

A solution of diethyl 2-benzyloxycarbonylaminomalonate (50 g) in anhydrous DMF (300 mL) was added portionwise with sodium hydride (60%, 6.47 g) with ice cooling and stirring, then the mixture was stirred at room temperature for 30 minutes, and subsequently added with ethyl 2-bromoacetate (22.6 g), and the mixture was stirred overnight. The reaction mixture was poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, in which elution was performed with n-hexane/ethyl acetate (5:1) for purification, and then crystallized from ethyl acetate/n-hexane to obtain the title compound (46.7 g, yield: 83%) as colorless crystals.

Example 3

Production of 1-ethyl hydrogen 3-benzyloxycarbonylamino-3-ethoxycarbonylsuccinate (hydrolysis reaction of ester)

(a) Purification of Enzyme

*Bacillus thuringiensis* NBRC 13866 provided by the independent administrative agency, National Institute of Technology and Evaluation, Biological Resource Center, Culture Collection Division was aerobically cultured in the GPY medium (medium comprising 1% glucose, 0.5% peptone and 0.3% yeast extract) at 30° C. for 16 hours. Wet cells were collected from the resulting culture by centrifugation (12,000×g, 10 minutes), and suspended in a 0.01 M Tris-hydrochloric acid buffer (pH 8.0). The suspension was subjected to ultrasonication using an ultrasonic homogenizer (NIPPON SEIKI, US-300T) under ice cooling, and then separated into supernatant and residue by centrifugation (12,000×g, 10 minutes). The supernatant was added with ammonium sulfate at a 20% saturated concentration under ice cooling, the mixture was stirred and then centrifuged (12,000×g, 10 minutes), and the supernatant was removed. The precipitates were suspended in a 0.01 M Tris-hydrochloric acid buffer (pH 8.0) containing 1 mM dithiothreitol (DTT), and dialyzed against the same buffer. This solution was added with DEAE Sepharose Fast Flow (GE Healthcare), they were mixed, and the mixture was filtered to collect an active solution.

The solution was added with 3-[(3-chloroamidopropyl)dimethylammonio]-propanesulfonate (CHAPS) at a final concentration of 1%, they were mixed, the mixture was subjected to a treatment with an ultrasonic homogenizer for 30 minutes under ice cooling, and then applied to DEAE Sepharose equilibrated with a 0.01 M Tris-hydrochloric acid buffer (pH 8.0) containing 1 mM DTT and 1% CHAPS (henceforth referred to as buffer A), washing was performed with the buffer A, and then proteins were eluted with a gradient of 0 to 0.3 M sodium chloride. The active fraction was dialyzed to remove CHAPS, and added with polyoxyethylene lauryl ether (Brij 35) at a final concentration of 0.05%, and applied to Phenyl Sepharose High Performance (GE Healthcare) equilibrated with a 0.01 M Tris-hydrochloric acid buffer (pH 8.0) containing 0.05% Brij 35, 1 mM DTT and 0.3 M sodium chloride (henceforth referred to as buffer B), washing was performed with the buffer B, and then proteins were eluted with a gradient of 0.3 to 0 M sodium chloride. The active fraction was dialyzed against the buffer A, concentrated by ultrafiltration, and applied to Mono Q (GE Healthcare) equilibrated with the buffer A, washing was performed with the buffer A, and then proteins were eluted with a gradient of 0 to 0.5 M sodium chloride. The active fraction was applied to Benzamidine Sepharose 4 Fast Flow (GE Healthcare) equilibrated with the buffer A, washing was performed with the buffer A, and then proteins were eluted with a gradient of 0 to 0.5 M sodium chloride. When the active fraction was subjected to SDS-PAGE (12% polyacrylamide gel containing 0.1% sodium dodecylsulfate), only a protein of about 50 kDa was confirmed, and thus purification of the objective enzyme was confirmed.

The activity was measured as follows. A solution containing the enzyme (0.1 mL) was added with 0.3 mL of purified water, 0.05 mL of a 1 M phosphate buffer (pH 7), and 0.05 mL of acetonitrile containing 1% diethyl 2-benzyloxycarbonylamino-2-ethoxycarbonylsuccinate, they were mixed, and then the mixture was shaken at 30° C. for 4 hours. The product in the reaction mixture, 1-ethyl hydrogen 3-benzyloxycarbonylamino-3-ethoxycarbonylsuccinate, was analyzed by HPLC. The activity for converting 1 μmol of the substrate per 1 minute was defined as 1 U.

(b) Reaction with Partially Purified Enzyme

The active fraction obtained by the DEAE Sepharose column purification of (a) mentioned above was concentrated by using an ultrafiltration membrane. The concentrate (0.08 mL, about 8 mU), 0.01 mL of acetonitrile containing 35% diethyl 2-benzyloxycarbonylamino-2-ethoxycarbonylsuccinate, and 0.01 mL of a 1 M phosphate buffer (pH 7) were mixed, and the mixture was shaken at 30° C. The reaction mixture was adjusted to pH 7.5 with 1 N sodium hydroxide. After 30 hours, it was confirmed by HPLC analysis that 1-ethyl hydrogen 3-benzyloxycarbonylamino-3-ethoxycarbonylsuccinate was obtained at a reaction yield of 70%. The optical purity of the product was confirmed by HPLC, and it was found that the product was the R-isomer, and the optical purity thereof was 100% ee.

$^1$H NMR (CDCl$_3$) δ (ppm): 7.35 (5H, m), 6.51 (1H, s), 5.09 (2H, m), 4.24 (2H, q, J=7.2 Hz), 4.08 (2H, q, J=7.2 Hz), 3.48 (2H, s), 1.19 (6H, m)

MS (FAB): m/z 368 (M+H$^+$)

HR-MS (FAB): calcd for C$_{17}$H$_{22}$NO$_8$ 368.1345, found 368.1314 (M+H$^+$)

(c) N-Terminus Amino Acid Sequence Analysis of Purified Enzyme

N-Terminus amino acid sequence analysis of the enzyme purified in (a) mentioned above was conducted. The analysis was entrusted to APRO Life Science Institute, Inc. (124-4, Aza-Itayashima, Seto-cho, Naruto-shi, Tokushima-ken, 771-0360, Japan). As a result of the analysis, a sequence of Glu-Lys-Lys-Pro-Val-Ser-Leu-Thr-Glu-Arg-Thr-Ser-Leu-Phe-Phe was obtained. Homology search for this sequence was performed in DNA Data Bank of Japan (DDBJ), and homology was observed with a hydrolase (accession no. C3IAP1) deduced from the gene sequence of *Bacillus thuringiensis* IBL 200.

(d) Acquisition of Gene

The enzyme gene was obtained from *Bacillus thuringiensis* NBRC 13866 on the basis of the gene information of this hydrolase. The *Bacillus thuringiensis* NBRC 13866 was cultured in 5 mL of the GPY medium at 30° C. for 24 hours with shaking at 200 rpm, and then genomic DNA was isolated from the culture by using Genomic DNA Buffer Set (QIAGEN N.V.) and QIAGEN Genomic-tip 500/G (QIAGEN N.V.), and used as a template together with 5'-TAAATCCATTGCTTAACGCCTCTACTCTT (Hokkiado System Science Co., Ltd.) and 5'-TCACGCAATGATGATTGCATGATGGCTTT (Hokkiado System Science Co., Ltd.) as primers to perform PCR using KOD-plus- (Toyobo Co., Ltd.) according to the protocol of the attached instruction. The PCR product was inserted into pUC18 (Takara Bio Inc.) to construct a plasmid (pBTEST7).

The nucleotide sequence of the inserted DNA was analyzed by the primer walking method using pBTEST7 as the template. For the nucleotide sequence analysis, ABI PRISM 310NT Genetic Analyzer (Applied Biosystems Japan, Inc.) and BigDye Terminator v3.1 Cycle Sequencing Kit (Applied Biosystems Japan, Inc.) were used, and the analysis was performed according to the protocols of the attached instructions of these equipments. As a result of the sequence analysis, it was found that the gene consisted of 1380 bp (SEQ ID NO: 1). The gene shown in SEQ ID NO: 1 encoded an enzyme consisting of 460 amino acid residues (SEQ ID NO: 2). Further, when homology search was performed for the sequence of SEQ ID NO: 2 in DDBJ, the highest homology was observed with a hydrolase deduced from the gene sequence of the *Bacillus thuringiensis* IBL 200 mentioned above. However, complete agreement was not observed, and the homology was found to be 96%.

Further, on the basis of the elucidated full length amino acid sequence of the enzyme as the body of the activity, it was found that the protein of which esterase activity was confirmed in (b) mentioned above was a protein comprising the amino acid sequence, wherein N-terminus 40 amino acid residues in the amino acid sequence shown in SEQ ID NO: 2 were deleted.

(e) Production of Recombinant *Escherichia Coli*

PCR was performed by using KOD-plus- with pBTEST7 as a template, as well as 5'-AAACAGCATGCAAAAAAAGAAATTACAAAAATCAGCAC (Hokkiado System Science Co., Ltd.) and 5'-CTTTTGTTGTAGATCTTTTCTTTGTCGCATTGACCCA (Hokkaido System Science Co., Ltd.) as primers. The PCR product was digested with SphI (Toyobo Co., Ltd.) and BglII (Toyobo Co., Ltd.), and inserted into pQE-70 (QIAGEN N.V.) at the SphI-BglII site to construct a plasmid (pBTEST12). Gene transfer was performed by incorporating pBTEST12 into the *Escherichia coli* JM109 using Competent High JM109 (Toyobo Co., Ltd.) according to the protocol of the attached instructions to produce *Escherichia coli* JM109/pBTEST12.

(f) Reaction Using Recombinant *Escherichia coli*

The *Escherichia coli* JM109/pBTEST12 produced in (e) mentioned above was inoculated into 5 mL of the LB liquid medium (1.0% polypeptone, 0.5% yeast extract, 1.0% sodium chloride, pH 7.0) containing 100 mg/L of sodium ampicillin (Wako Pure Chemical Industries Co., Ltd.), and cultured at 25° C. for 12 hours with shaking at 200 rpm. This culture was subcultured into 200 mL of the LB liquid medium containing 0.1 mM isopropyl-β-thiogalactopyranoside (Nakarai Tesque Inc.), and culture was performed at 25° C. for 24 hours with shaking at 200 rpm. The culture was prepared in a volume of 1.6 L, and centrifuged at 12,000×g and 4° C. for 10 minutes to obtain cells. The cells were suspended in purified water, the suspension was added with 10 mL of a solution containing 35% diethyl 2-benzyloxycarbonylamino-2-ethoxycarbonylsuccinate in acetonitrile and 10 mL of a 1.0 M phosphate buffer (pH 7.0), and the mixture was further added with purified water to a total volume of 100 mL. This solution was maintained at 25° C. for 24 hours with stirring. The reaction mixture was timely added with a 28% sodium hydroxide solution so that pH of the mixture was maintained to be 7.0.

This reaction mixture was centrifuged at 12,000×g and 4° C. for 10 minutes, the cells were removed, and then the supernatant was analyzed by HPLC. As a result, it was confirmed that 1-ethyl hydrogen 3-benzyloxycarbonylamino-3-ethoxycarbonylsuccinate was obtained at a reaction yield of 90%. The optical purity of the product was confirmed by HPLC, and it was found that the product was the R-isomer, and the optical purity thereof was 100% ee.

(g) Purification of Enzyme from Recombinant *Escherichia coli* and Reaction Using Obtained Purified Enzyme The *Escherichia coli* JM109/pBTEST12 was inoculated into 5 mL of the LB liquid medium containing 100 mg/L of sodium ampicillin, and cultured at 25° C. for 12 hours with shaking at 200 rpm. This culture was subcultured into 200 mL of the LB liquid medium containing 0.1 mM isopropyl-β-thiogalactopyranoside, and culture was performed at 25° C. for 24 hours with shaking at 200 rpm. The enzyme was purified from this culture by using QIAexpress Type ATG Kit (QIAGEN N.V.) according to the protocol of the attached instructions. The purified enzyme solution was subjected to electrophoresis with SDS-PAGE (12% polyacrylamide gel containing 0.1% sodium dodecylsulfate). As a result, a single band was observed, and thus it was confirmed that the enzyme was successfully purified.

By using this purified enzyme, a solution was prepared in a composition of 3% diethyl 2-benzyloxycarbonylamino-2-ethoxycarbonylsuccinate, 0.1 M phosphate buffer (pH 7.0), and 0.55 mg/mL of the purified enzyme, and left at 30° C. for 3 hours. Then, the reaction mixture was analyzed by HPLC, and it was confirmed that 1-ethyl hydrogen 3-benzyloxycarbonylamino-3-ethoxycarbonylsuccinate was successfully obtained at a reaction yield of 20%. Further, the optical purity of the product was confirmed by HPLC, and it was found that the product was the R-isomer, and the optical purity thereof was 100% ee.

(h) Production of Recombinant *Escherichia coli* Expressing N-Terminus-Deleted Enzyme Gene It was found in (d) mentioned above that the protein having the esterase activity was a protein comprising the amino acid sequence, wherein N-terminus 40 amino acid residues in the amino acid sequence shown in SEQ ID NO: 2 were deleted. Therefore, a recombinant *Escherichia coli* that expressed the protein of which N-terminus was deleted was produced.

PCR was performed by using KOD-plus- together with pBTEST12 as a template, as well as 5'-GTACAAAGCATGCAAAAGAAACCAGTCTCTTTAACGG AGCG (Hokkaido System Science Co., Ltd.) and 5'-CTTTTGTTGTAGATCTTTTCTTTGTCGC ATTGACCCA (Hokkaido System Science Co., Ltd.) as primers. The PCR product was digested with SphI and BglII, and inserted into pQE-70 at the SphI-BglII site to construct a plasmid (pBTEST38). Gene transfer was performed by incorporating pBTEST38 into *Escherichia coli* JM109 using Competent High JM109 according to the protocol of the attached instructions to produce *Escherichia coli* JM109/pBTEST38.

The *Escherichia coli* JM109/pBTEST38 was inoculated into 5 mL of the LB liquid medium containing 100 mg/L of sodium ampicillin, and cultured at 30° C. for 19 hours with shaking at 200 rpm. The resulting culture was subcultured into 100 mL of the LB liquid medium containing 0.1 mM isopropyl-6-thiogalactopyranoside, and culture was performed at 25° C. for 16 hours with shaking at 200 rpm.

The culture was prepared in a volume of 3 L, and centrifuged at 12,000×g and 4° C. for 10 minutes to obtain cells. The cells were suspended in a small volume of a 0.1 M phosphate buffer (pH 7.0), the suspension was added with 15 mL of a solution containing 35% diethyl 2-benzyloxycarbonylamino-2-ethoxycarbonylsuccinate in acetonitrile, and the mixture was further added with purified water to a total volume of 150 mL. This solution was maintained at 25° C. for 18 hours with stirring. The reaction mixture was timely added with a 28% sodium hydroxide solution so that pH of the mixture was maintained to be 7.0.

This reaction mixture was centrifuged at 12,000×g and 4° C. for 10 minutes, the cells were removed, and then the supernatant was analyzed by HPLC. As a result, it was confirmed that 1-ethyl hydrogen 3-benzyloxycarbonylamino-3-ethoxycarbonylsuccinate was successfully obtained at a reaction yield of 90%. The optical purity of the product was confirmed by HPLC, and it was found that the product was the R-isomer, and the optical purity thereof was 100% ee.

Example 4

Production of (R)-diethyl 2-benzyloxycarbonylamino-2-carbamoylsuccinate

A solution of (R)-1-ethyl hydrogen 3-benzyloxycarbonylamino-3-ethoxycarbonylsuccinate (1.8 g) in THF (20 mL) was added with triethylamine (0.96 mL) and isobutyl chloroformate (0.84 mL, 0.87 g) in this order at −15° C. with stirring, and the mixture was stirred for 5 minutes. A solution of 25% aqueous ammonia (0.47 mL) was dropped into the reaction mixture at the same temperature. The reaction mixture was stirred at the same temperature for 1 hour, and then poured into diluted hydrochloric acid, the mixture was extracted with ethyl acetate, and the extract was dried over anhydrous magnesium sulfate. The solvent was evaporated under reduced pressure, and the residue was subjected to silica gel column chromatography, in which elution was performed with n-hexane/ethyl acetate (1:1) for purification, and then crystallized from ethyl acetate/n-hexane to obtain the title compound (1.51 g, yield: 84%) as colorless crystals. Optical rotation $[\alpha]_D^{25}$ was −5.7° (c 0.52, ethanol) and optical purity was 96.1% ee.

$^1$H NMR (CDCl$_3$) δ (ppm): 7.34 (5H, m), 6.51 (1H, br), 6.35 (1H, br), 5.63 (1H, br), 5.12 (2H, s), 4.26 (2H, m), 4.10 (2H, q, J=7.2 Hz), 3.48 (2H, s), 1.23 (6H, m)

MS (FAB): 367 (M+H$^+$)

HR-MS (FAB): calcd for C$_{17}$H$_{23}$N$_2$O$_7$ 367.1505, found 367.1509 (M+H$^+$)

Example 5

Production of (R)-2-benzyloxycarbonylamino-2-ethoxycarbonylsuccinimide

A solution of (R)-diethyl 2-benzyloxycarbonylamino-2-carbamoylsuccinate (200 mg) in dehydrated ethanol (10 mL) was added with sodium ethoxide (41 mg) with ice cooling and stirring, the mixture was stirred at the same temperature for 2 hours, then cold 1 mol/L hydrochloric acid was poured into the mixture, and the mixture was extracted with ethyl acetate. The extract was washed with saturated brine, and then dried over anhydrous magnesium sulfate. The solvent was evaporated under reduced pressure, and the residue was recrystallized from ethyl acetate/n-hexane to obtain the title compound (149 mg, yield: 85%) as colorless crystals. Optical rotation $[\alpha]_D^{28}$ was −31.8° (c 0.59, ethanol), and optical purity was 99.2% ee.

$^1$H NMR (CDCl$_3$) δ (ppm): 8.39 (1H, s), 7.36 (5H, m), 6.27 (1H, s), 5.12 (2H, m), 4.32 (2H, q, J=6.9 Hz), 3.18 (2H, m), 1.29 (3H, t, J=7.1 Hz)

MS (FAB): 321 (M+H$^+$)

HR-MS (FAB): calcd for C$_{15}$H$_{17}$N$_2$O$_6$ 321.1087, found 321.1074 (M+H$^+$)

Example 6

Production of (R)-2-amino-2-ethoxycarbonylsuccinimide (R)-2-Benzyloxycarbonylamino-2-ethoxycarbonylsuccinimide (80 mg) was dissolved in ethanol (10 mL), the solution was added with 5% palladium/carbon (4 mg), and catalytic hydrogenation was performed at room temperature under a hydrogen atmosphere. After the catalyst was removed by filtration, the filtrate was concentrated under reduced pressure. The residue was recrystallized from ethanol to obtain the title compound (43 mg, yield: 93%) as colorless crystals. Optical rotation $[\alpha]_D^{24}$ was −35.9° (c 0.22, ethanol). Optical purity was more than 99.9% ee.

1H NMR (CDCl$_3$) δ (ppm): 4.28 (2H, q, J=7.2 Hz), 3.19 (1H, d, J=18.0 Hz), 2.74 (1H, d, J=18.0 Hz), 1.30 (3H, t, J=7.1 Hz)

MS (FAB): 187 (M+H$^+$)

HR-MS (FAB): calcd for C$_7$H$_{11}$N$_2$O$_4$ 187.0719, found 187.0700 (M+H$^+$)

INDUSTRIAL APPLICABILITY

According to the present invention, as a process for efficiently producing optically active succinimide derivatives as key intermediates of the compound A, which is useful as a therapeutic agent for diabetic complications, there is provided a process for efficiently producing optically active carboxylic acid derivatives from ester derivatives which are also useful intermediates of the compound A.

What is claimed is:

1. A process for producing an optically active succinimide derivative represented by the formula (I):

[Formula I]

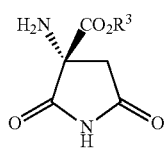

(I)

[in the formula (I), R³ represents a lower alkyl] or a salt thereof, which comprises the following steps (A) to (D), and further comprises the step (E), if necessary:

(A) the step of reacting an aminomalonate derivative represented by the formula (II):

[Formula II]

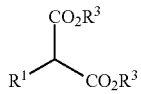

(II)

[in the formula (II), R¹ represents amino or an amino protected with a protective group, and two of R³ represent the same lower alkyls having the same meaning as that defined above] and a halogenated acetic acid ester derivative represented by the formula (III):

[Formula III]

$Y-CH_2CO_2R^2$ (III)

[in the formula (III), R² represents a lower alkyl, and Y represents a halogen] in the presence of a base for conversion into an ester derivative represented by the formula (IV):

[Formula IV]

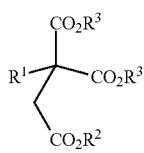

(IV)

[in the formula (IV), each of R¹, R², and R³ has the same meaning as that defined above] or a salt thereof, (B) the step of allowing a non-animal-derived enzyme, an isolated host cell that produces the enzyme, a culture of the cell, or a processed product of the cell or a culture of the cell to react on the ester derivative represented by the formula (IV) or a salt thereof for conversion into an optically active carboxylic acid derivative represented by the formula (V):

[Formula V]

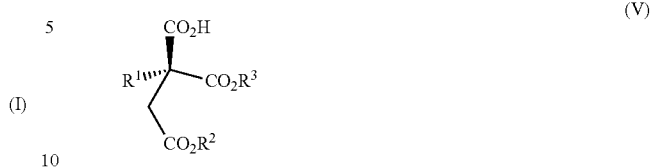

[in the formula (V), each of R¹, R², and R³ has the same meaning as that defined above] or a salt thereof, wherein the non-animal-derived enzyme is a protein selected from the following (a) to (d):

(a) a protein identified by the amino acid sequence shown in SEQ ID NO: 2, (b) a homolog of the protein of (a), wherein the homolog (i) consists of an amino acid sequence having 95% or more identity to the amino acid sequence shown in SEQ ID NO: 2 and (ii) has an esterase activity similar to that of the protein of (a), (c) a protein comprising the amino acid sequence shown in SEQ ID NO: 2, except that 1 to 40 amino acid residues from the N-terminus of the amino acid sequence shown in SEQ ID NO: 2 are deleted, and (d) a homolog of the protein of (a), wherein the homolog (i) consists of an amino acid sequence having 95% or more identity to the amino acid sequence shown in SEQ ID NO: 2, except that 1 to 40 amino acid residues from the N-terminus of the amino acid sequence shown in SEQ ID NO: 2 are deleted, and (ii) has an esterase activity similar to that of the protein of (a), (C) the step of reacting the optically active carboxylic acid derivative represented by the formula (V) or a salt thereof with an ammonia source in the presence of a condensing agent, or reacting the optically active carboxylic acid derivative represented by the formula (V) or a salt thereof with an activating reagent and then reacting the resultant with an ammonia source, for conversion into an optically active amide derivative represented by the formula (VI):

[Formula 6]

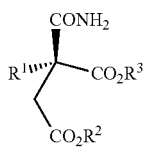

(VI)

[in the formula (VI), each of R¹, R², and R³ has the same meaning as that defined above] or a salt thereof, (D) the step of allowing a base to react on the optically active amide derivative represented by the formula (VI) or a salt thereof for conversion into an optically active succinimide derivative represented by the formula (I) or (VII):

[Formula 7]

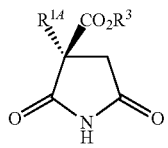

(VII)

[in the formula (VII), $R^{1A}$ represents an amino protected with a protective group, and $R^3$ has the same meaning as that defined above] or a salt thereof, and (E) the step of eliminating the protective group on $R^{1A}$ of the optically active succinimide derivative represented by the formula (VII) or a salt thereof for conversion into an optically active succinimide derivative represented by the formula (I) or a salt thereof.

2. A process for producing an optically active carboxylic acid derivative represented by the formula (V):

[Formula V]

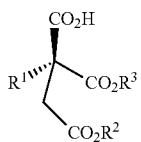

(V)

[in the formula (V), $R^1$ represents amino or an amino protected with a protective group, and $R^2$ and $R^3$ represent a lower alkyl] or a salt thereof, which comprises the step of allowing a non-animal-derived enzyme, an isolated host cell that produces the enzyme, a culture of the cell, or a processed product of the cell or a culture of the cell to react on an ester derivative represented by the formula (IV):

[Formula IV]

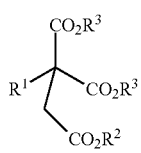

(IV)

[in the formula (IV), each of $R^1$, $R^2$, and $R^3$ has the same meaning as that defined above] or a salt thereof,
wherein the non-animal-derived enzyme is a protein selected from the following (a) to (d):
(a) a protein identified by the amino acid sequence shown in SEQ ID NO: 2,
(b) a homolog of the protein of (a), wherein the homolog (i) consists of an amino acid sequence having 95% or more identity to the amino acid sequence shown in SEQ ID NO: 2 and (ii) has an esterase activity similar to that of the protein of (a),
(c) a protein comprising the amino acid sequence shown in SEQ ID NO: 2, except that 1 to 40 amino acid residues from the N-terminus of the amino acid sequence shown in SEQ ID NO: 2 are deleted, and
(d) a homolog of the protein of (a), wherein the homolog (i) consists of an amino acid sequence having 95% or more identity to the amino acid sequence shown in SEQ ID NO: 2, except that 1 to 40 amino acid residues from the N-terminus of the amino acid sequence shown in SEQ ID NO: 2 are deleted, and (ii) has an esterase activity similar to that of the protein of (a).

3. The production process according to claim 1, wherein $R^1$ and $R^{1A}$ are benzyloxycarbonylamino groups, $R^2$ is ethyl, and $R^3$ is ethyl.

4. A process for producing (3R)-2'-(4-bromo-2-fluorobenzyl)spiro{pyrrolidine-3,4'(1'H)-pyrrolo[1,2-a]pyrazine}-1', 2',3',5(2'H)-tetraone (compound A), which comprises the step of producing an optically active succinimide derivative represented by the formula (I) (compound I) by the production process according to claim 1, and the step of converting the compound (I) obtained in the above step into the compound A.

5. A process for producing (3R)-2'-(4-bromo-2-fluorobenzyl)spiro{pyrrolidine-3,4'(1'H)-pyrrolo[1,2-a]pyrazine}-1', 2',3',5(2'H)-tetraone (compound A), which comprises the following steps (a) to (e):
(a) the step of producing an optically active succinimide derivative represented by the formula (I) (compound I) by the method according to claim 1;
(b) the step of reacting the compound (I) obtained in the step (a) with 2,5-dimethoxytetrahydrofuran in the presence of an acid;
(c) the step of reacting the product obtained in the step (b) with a trichloroacetylating reagent;
(d) the step of reacting the product obtained in the step (c) with 4-bromo-2-fluorobenzylamine; and
(e) the step of isolating the compound A obtained in the step (d).

6. The production process according to claim 4, wherein $R^3$ is ethyl.

7. The production process according to claim 2, wherein $R^1$ and $R^{1A}$ are benzyloxycarbonylamino groups, $R^2$ is ethyl, and $R^3$ is ethyl.

8. The production process according to claim 5, wherein $R^3$ is ethyl.

9. The production process according to claim 5, wherein the acid is acetic acid.

10. The production process according to claim 5, wherein the trichloroacetylating reagent is selected from the group consisting of trichloroacetyl chloride, trichloroacetyl bromide, and trichloroacetic anhydride.

11. The production process according to claim 1, wherein the non-animal-derived enzyme is (a) a protein identified by the amino acid sequence shown in SEQ ID NO: 2.

12. The production process according to claim 1, wherein the non-animal-derived enzyme is (b) a homolog of the protein of (a), wherein the homolog (i) consists of an amino acid sequence having 95% or more identity to the amino acid sequence shown in SEQ ID NO: 2 and (ii) has an esterase activity similar to that of the protein of (a).

13. The production process according to claim 1, wherein the non-animal-derived enzyme is (c) a protein comprising the amino acid sequence shown in SEQ ID NO: 2, except that 1 to 40 amino acid residues from the N-terminus of the amino acid sequence shown in SEQ ID NO: 2 are deleted.

14. The production process according to claim 1, wherein the non-animal-derived enzyme is (d) a homolog of the protein of (a), wherein the homolog (i) consists of an amino acid sequence having 95% or more identity to the amino acid sequence shown in SEQ ID NO: 2, except that 1 to 40 amino acid residues from the N-terminus of the amino acid sequence shown in SEQ ID NO: 2 are deleted, and (ii) has an esterase activity similar to that of the protein of (a).

15. The production process according to claim 2, wherein the non-animal-derived enzyme is (a) a protein identified by the amino acid sequence shown in SEQ ID NO: 2.

16. The production process according to claim 2, wherein the non-animal-derived enzyme is (b) a homolog of the protein of (a), wherein the homolog (i) consists of an amino acid sequence having 95% or more identity to the amino acid sequence shown in SEQ ID NO: 2, and (ii) has an esterase activity similar to that of the protein of (a).

17. The production process according to claim 2, wherein the non-animal-derived enzyme is (c) a protein comprising the amino acid sequence shown in SEQ ID NO: 2, except that 1 to 40 amino acid residues from the N-terminus of the amino acid sequence shown in SEQ ID NO: 2 are deleted.

18. The production process according to claim 2, wherein the non-animal-derived enzyme is (d) a homolog of the protein of (a), wherein the homolog (i) consists of an amino acid sequence having 95% or more identity to the amino acid sequence shown in SEQ ID NO: 2, except that 1 to 40 amino acid residues from the N-terminus of the amino acid sequence shown in SEQ ID NO: 2 are deleted, and (ii) has an esterase activity similar to that of the protein of (a).

* * * * *

SEQUENCE LISTING

<160> NUMBER OF SEQ ID NOS: 9

<210> SEQ ID NO 1
<211> LENGTH: 1380
<212> TYPE: DNA
<213> ORGANISM: Bacillus thuringiensis

<400> SEQUENCE: 1

```
atgaaaaaaa agaaattaca aaaatcagca cttctttttg ccttactctt ttctttaggt      60
gtttcttctt tctcacttat aacgaagatt catgcagaca cacaagaggt acaaactgca     120
gaaaagaaac cagtctcttt aacggagcgt acgtctttat ttttgaata tctccagcaa      180
gataaatatt cagaggcact acaattgacg tctgctgctt tcaatccaa gtttacggca      240
aacatattac aaaactggtg gacacaaagt ggcgggagca ggattacaag catgggaaca     300
cctgttatta agaacgaaa catagtccat caaacggttg aaattccagg agctatcgaa      360
ggaactacta ttccactact ccttaaattc acgcctggtg gcaaagttga tgaagttggc     420
gtaaggacga cgccacagaa atcttatacc atcccgcatc ctagttatga ccaacctgat     480
tcctaccaag aacgtgaaat cgtaattgga aatactacat acccgttacc agccacatta     540
acggttccaa aacataaacc tggcgaaaaa gtacctgttg ttgttcttgt tcacggttct    600
ggtccacaag atcgtgacag tacatttatg ggagctaaaa tctttagaga ccttgcagct     660
ggtctttcat caagggggtat cgcagtgcta cgttacgaga acgttccttt agaacacggt    720
tttaaaatga ctgcagaacc tgctacatta gacagcgata ctacagatga tgccatatat    780
gcagcaaatt cagcagcgca gcaggaaggt attgacccag ataacatttt cattctcgga    840
catagccaag gtgctggcac catgccacgt atactaagca agcaccttc atcacttgta     900
agaggaagta ttttaatggc accacctgca cgtcctttta ctgacatgct ccttgatcag    960
tatcagtacc ttggggcacc aaaggagtat attgatgaac taaaaaaca attcgcttat   1020
attgaggatc ctacttttaa tccagatcac ccaccagccg ttataatta tctttctcca    1080
catttcatgt atgatgtgac ccgttggcat ccagttgagg aagcgaaatc acgaaaagag   1140
ccattactga ttctacaagg ctcacgtgat tatcaagtaa cggtaaaaga agagtttacg   1200
agatggcaag aaggtctttc aagtcgcagt aatgttcagt ttaaagaata tccgaaattg    1260
aatcacctct tcacggaggg cgacggtgaa ttaagtcacc ctagtgaata cgaagtccct    1320
tcaaatgttc cagcgtatgt catccaggac atcgctacat gggtcaatgc gacaaagaaa    1380
```

<210> SEQ ID NO 2
<211> LENGTH: 460
<212> TYPE: PRT
<213> ORGANISM: Bacillus thuringiensis

<400> SEQUENCE: 2

```
Met Lys Lys Lys Leu Gln Lys Ser Ala Leu Ser Phe Ala Leu Leu
1               5                   10                  15

Phe Ser Leu Gly Val Ser Ser Phe Ser Leu Ile Thr Lys Ile His Ala
                20                  25                  30

Asp Thr Gln Glu Val Gln Thr Ala Glu Lys Lys Pro Val Ser Leu Thr
            35                  40                  45

Glu Arg Thr Ser Leu Phe Phe Glu Tyr Leu Gln Gln Asp Lys Tyr Ser
        50                  55                  60

Glu Ala Leu Gln Leu Thr Ser Ala Ala Phe Gln Ser Lys Phe Thr Ala
65                  70                  75                  80

Asn Ile Leu Gln Asn Trp Trp Thr Gln Ser Gly Gly Ser Arg Ile Thr
                85                  90                  95

Ser Met Gly Thr Pro Val Ile Lys Glu Arg Asn Ile Val His Gln Thr
            100                 105                 110

Val Glu Ile Pro Gly Ala Ile Glu Gly Thr Thr Ile Pro Leu Leu Leu
        115                 120                 125
```

-continued

```
Lys Phe Thr Pro Gly Gly Lys Val Asp Glu Val Gly Val Arg Thr Thr
            130                 135                 140

Pro Gln Lys Ser Tyr Thr Ile Pro His Pro Ser Tyr Asp Gln Pro Asp
145                 150                 155                 160

Ser Tyr Gln Glu Arg Glu Ile Val Ile Gly Asn Thr Thr Tyr Pro Leu
                165                 170                 175

Pro Ala Thr Leu Thr Val Pro Lys His Lys Pro Gly Glu Lys Val Pro
            180                 185                 190

Val Val Val Leu Val His Gly Ser Gly Pro Gln Asp Arg Asp Ser Thr
        195                 200                 205

Phe Met Gly Ala Lys Ile Phe Arg Asp Leu Ala Ala Gly Leu Ser Ser
210                 215                 220

Arg Gly Ile Ala Val Leu Arg Tyr Glu Lys Arg Ser Leu Glu His Gly
225                 230                 235                 240

Phe Lys Met Thr Ala Glu Pro Ala Thr Leu Asp Ser Asp Thr Thr Asp
                245                 250                 255

Asp Ala Ile Tyr Ala Ala Asn Ser Ala Ala Gln Gln Glu Gly Ile Asp
                260                 265                 270

Pro Asp Asn Ile Phe Ile Leu Gly His Ser Gly Gly Ala Gly Thr Met
            275                 280                 285

Pro Arg Ile Leu Ser Lys Ala Pro Ser Ser Leu Val Arg Gly Ser Ile
290                 295                 300

Leu Met Ala Pro Pro Ala Arg Pro Phe Thr Asp Met Leu Leu Asp Gln
305                 310                 315                 320

Tyr Gln Tyr Leu Gly Ala Pro Lys Glu Tyr Ile Asp Glu Leu Lys Lys
                325                 330                 335

Gln Phe Ala Tyr Ile Glu Asp Pro Thr Phe Asn Pro Asp His Pro Pro
            340                 345                 350

Ala Gly Tyr Asn Tyr Leu Ser Pro His Phe Met Tyr Asp Val Thr Arg
            355                 360                 365

Trp His Pro Val Glu Glu Ala Lys Ser Arg Lys Glu Pro Leu Leu Ile
370                 375                 380

Leu Gln Gly Ser Arg Asp Tyr Gln Val Thr Val Lys Glu Glu Phe Thr
385                 390                 395                 400

Arg Trp Gln Glu Gly Leu Ser Ser Arg Ser Asn Val Gln Phe Lys Glu
                405                 410                 415

Tyr Pro Lys Leu Asn His Leu Phe Thr Glu Gly Asp Gly Glu Leu Ser
            420                 425                 430

His Pro Ser Glu Tyr Glu Val Pro Ser Asn Val Pro Ala Tyr Val Ile
            435                 440                 445

Gln Asp Ile Ala Thr Trp Val Asn Ala Thr Lys Lys
450                 455                 460

<210> SEQ ID NO 3
<211> LENGTH: 15
<212> TYPE: PRT
<213> ORGANISM: Bacillus thuringiensis

<400> SEQUENCE: 3

Glu Lys Lys Pro Val Ser Leu Thr Glu Arg Thr Ser Leu Phe Phe
1               5                   10                  15

<210> SEQ ID NO 4
<211> LENGTH: 29
<212> TYPE: DNA
```

```
<213> ORGANISM: Artificial sequence
<220> FEATURE:
<223> OTHER INFORMATION: Synthetic Sequence

<400> SEQUENCE: 4
taaatccatt gcttaacgcc tctactctt                                    29

<210> SEQ ID NO 5
<211> LENGTH: 29
<212> TYPE: DNA
<213> ORGANISM: Artificial sequence
<220> FEATURE:
<223> OTHER INFORMATION: Synthetic Sequence

<400> SEQUENCE: 5
tcacgcaatg atgattgcat gatggcttt                                    29

<210> SEQ ID NO 6
<211> LENGTH: 38
<212> TYPE: DNA
<213> ORGANISM: Artificial sequence
<220> FEATURE:
<223> OTHER INFORMATION: Synthetic Sequence

<400> SEQUENCE: 6
aaacagcatg caaaaaaga aattacaaaa atcagcac                            38

<210> SEQ ID NO 7
<211> LENGTH: 37
<212> TYPE: DNA
<213> ORGANISM: Artificial sequence
<220> FEATURE:
<223> OTHER INFORMATION: Synthetic Sequence

<400> SEQUENCE: 7
cttttgttgt agatcttttc tttgtcgcat tgaccca                            37

<210> SEQ ID NO 8
<211> LENGTH: 41
<212> TYPE: DNA
<213> ORGANISM: Artificial sequence
<220> FEATURE:
<223> OTHER INFORMATION: Synthetic Sequence

<400> SEQUENCE: 8
gtacaaagca tgcaaaagaa accagtctct ttaacggagc g                       41

<210> SEQ ID NO 9
<211> LENGTH: 37
<212> TYPE: DNA
<213> ORGANISM: Artificial sequence
<220> FEATURE:
<223> OTHER INFORMATION: Synthetic Sequence

<400> SEQUENCE: 9
cttttgttgt agatcttttc tttgtcgcat tgaccca                            37
```